United States Patent [19]

Ladduwahetty et al.

[11] Patent Number: 5,256,671
[45] Date of Patent: Oct. 26, 1993

[54] AZABICYCLIC COMPOUNDS, PHARMACEUTICAL COMPOSITIONS CONTAINING THEM AND THEIR USE IN THERAPY

[75] Inventors: Tamara Ladduwahetty, Buckhurst Hill; Christopher J. Swain, Duxford, both of England

[73] Assignee: Merck Sharp & Dohme, Limited, Hoddesdon, England

[21] Appl. No.: 905,974

[22] Filed: Jun. 29, 1992

[51] Int. Cl.$^5$ ................ A61K 31/435; C07D 453/02
[52] U.S. Cl. ................... 514/305; 514/214; 514/299; 514/413; 540/585; 540/477; 546/112; 546/133; 546/137; 548/453; 548/406
[58] Field of Search ............. 540/585, 477; 546/112, 546/133, 137; 548/453; 514/214, 299, 305, 413

[56] References Cited

FOREIGN PATENT DOCUMENTS

90/05729 5/1990 PCT Int'l Appl. .

OTHER PUBLICATIONS

Otsuka, et al., "Role Of Substance P As A Sensory Transmitter In Spinal Cord and Sympathetic Ganglia" 1982 Substance P in the Nervous System, CIBA Foundation Symposium 91, pp. 13–34.
TIPS, (Dec. 1987) 8, pp. 506–510.
B. E. B. Sandberg, et al., J. Med. Chem. 1982, 25, 1009.
Levine, et al. Science, 1984 226, pp. 547–549.
Mantyh, et al:, Neuroscience, 1988 25 (3) pp. 817–837.
D. Regoli, "Trends in Cluster Headache" Ed. Sicuteri, et al Elsevier Scientific Publishers 1987 p. 85.
Kidd, et al., The Lancet, Nov. 11, 1989 "A Neurogenic Mechanism For Symmetrical Arthritis".
Gronblad, et al., "Neuropeptides In Synovium of Patients With Rheumatoid Arthritis & Osteoarthritis" J. Rheumatol 1988 15 (12) pp. 1807–1810.
O'Byrne, et al. Arthritis and Rheumatism 1990, 33, pp. 1023–1028.
Hamlet, et al. Can. J. Pharmacol. Physiol. 1988, 66, pp. 1361–1367.
Lotz, et al., Science 1988, 241, pp. 1218–1221.
Kimball, et al., J. Immunol. 1988, 141 (10) pp. 3564–3569.
Mantyh, et al. PNAS 1988, 85, pp. 3235–3239.
Yanker, et al. Science, 1990 350 pp. 279–282.

Primary Examiner—Cecilia Tsang
Attorney, Agent, or Firm—Robert J. North; Charles M. Caruso; Joseph F. DiPrima

[57] ABSTRACT

Compounds of formula (I), and salts and prodrugs thereof:

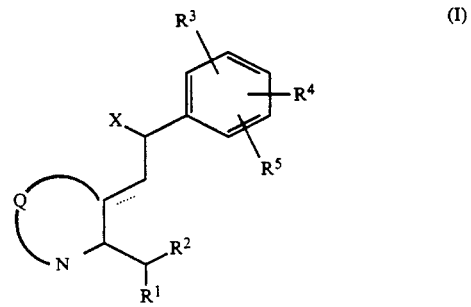

wherein
Q is the residue of an optionally substituted azabicyclic ring system;
the dotted line represents an optional double bond;
X represents H, —OH, =O or halo;
$R^1$ represents H, phenyl or thienyl, which phenyl or thienyl groups may be optionally substituted by halo or trifluoromethyl;
$R^2$ represents phenyl, thienyl or benzyl, any of which groups may be optionally substituted by halo or trifluoromethyl; and
$R^3$, $R^4$ and $R^5$ independently represent H, $C_{1-6}$ alkyl, $C_{2-6}$ alkenyl, $C_{2-6}$ alkynyl, halo, cyano, nitro, trifluoromethyl, trimethylsilyl, —OR$^a$, SR$^a$, SOR$^a$, SO$_2$R$^a$, —NR$^a$R$^b$, —NR$^a$COR$^b$, —NR$^a$CO$_2$R$^b$, —CO$_2$R$^a$ or —CONR$^a$R$^b$; and
R$^a$ and R$^b$ independently represent H, $C_{1-6}$ alkyl, phenyl or trifluoromethyl, are tachykinin receptor antagonists. They and compositions thereof are useful in therapy.

12 Claims, No Drawings

AZABICYCLIC COMPOUNDS, PHARMACEUTICAL COMPOSITIONS CONTAINING THEM AND THEIR USE IN THERAPY

This invention relates to a class of azabicyclic compounds, which are useful as tachykinin antagonists. More particularly, the compounds of the invention comprise an azabicyclic ring system substituted by an arylalkyl or arylalkenyl moiety and by a benzhydryl, or like, moiety.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:
Arg-Pro-Lys-Pro-Gln-Gln-Phe-Phe-Gly-Leu-Met-NH$_2$
Neurokinin A:
His-Lys-Thr-Asp-Ser-Phe-Val-Gly-Leu-Met-NH$_2$
Neurokinin B:
Asp-Met-His-Asp-Phe-Phe-Val-Gly-Leu-Met-NH$_2$ Substance P is believed inter alia to be involved in the neurotransmission of pain sensations [Otsuka et al, "Role of Subtance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (December 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817–37 and D. Regoli in "Trends in Cluster Headache" Ed. Sicuteri et al Elsevier Scientific Publishers, Amsterdam (1987) page 85)]. It is also hypothesised that there is a neurogenic mechanism for arthritis in which substance P may play a role [Kidd et al "Neurogenic Mechanism for Symmetrical Arthritis" in the Lancet, Nov. 11, 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and osteoarthritis [O'Byrne et al in Arthritis and Rheumatism (1990) 33 1023-8]. Other disease areas where tachykinin antagonists are belived to be useful are allergic conditions [Hamelet et al Can. J. Pharmacol. Physiol. (1988) 66 1361-7], immunoregulation [Lotz et al Science (1988) 241 1218-21 and Kimball et al, J. Immunol. (1988) 141 (10) 3564–9] vasodilation, bronchospasm, reflec or neuronal control of the viscera [Mantyh et al, PNAS (1988) 85 3235-9 ] and, possibly by arresting or slowing β-amyloid-mediated neurodengenerative changes [Yankner et al Science (1990) 250, 279–82] in senile dementia of the Alzheimer type, Alzheimer's disease and Down's Syndrome. Substance P may also play a role in demyelinating diseases such as multiple sclerosis and amyotrophic lateral sclerosis [J. Luber-Narod et. al., poster to be presented at C.I.N.P. XVIIIth Congress, Jun. 28th–Jul. 2nd, 1992, in press].

In view of their metabolic instability, peptide derivatives are likely to be limited utility as therapeutic agents. It is for this reason that non-peptide tachykinin antagonists are sought.

For example, WO-A-90/05729 describes inter alia a class of cis-3-[cyclic]methylamino-2-[(α-substituted)-arylmethyl]quinuclidine compounds which are stated to be useful as substance P antagonists for treating gastrointestinal disorders, central nervous system disorders, inflammatory diseases and pain or migraine. There is, however, no disclosure or suggestion in WO-A-90/05729 of the arylethyl-substituted azabicyclic derivatives provided by the present invention.

We have now found a further class of non-peptides which are potent antagonists of tachykinin receptors.

The present invention provides a compound of formula (I), or a salt or prodrug thereof:

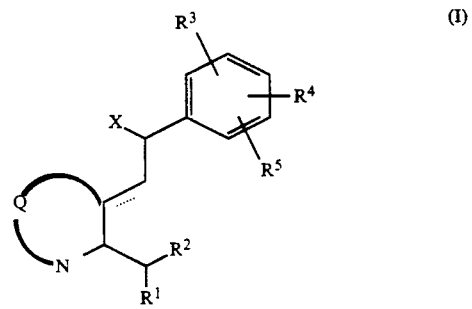

wherein
Q is the residue of an optionally substituted azabicyclic ring system;
the dotted line represents an optional double bond;
X represents H, —OH, =O or halo;
R$^1$ represents H, phenyl or thienyl, which phenyl or thienyl groups may be optionally substituted by halo or trifluoromethyl;
R$^2$ represents phenyl, thienyl or benzyl, any of which groups may be optionally substituted by halo or trifluoromethyl; and
R$^3$, R$^4$ and R$^5$ independently represent H, C$_{1-6}$ alkyl, C$_{2-6}$ alkenyl, C$_{2-6}$ alkynyl, halo, cyano, nitro, trifluoromethyl, trimethylsilyl, —OR$^a$, SR$^a$, SOR$^a$, SO$_2$R$^a$, —NR$^a$R$^b$, —NR$^a$COR$^b$, —NR$^a$CO$_2$R$^b$, —CO$_2$R$^a$ or —CONR$^a$R$^b$; and
R$^a$ and R$^b$ independently represent H, C$_{1-6}$ alkyl, phenyl or trifluoromethyl.

The azabicyclic ring system of which Q is the residue is a non-aromatic ring system containing, as the sole heteroatom, the nitrogen atom indicated in formula (I) above. Suitably the ring system contains from 6 to 10 ring atoms, preferably from 7 to 9 ring atoms. The azabicyclic ring system may be fused, spiro or bridged, preferably bridged. The azabicyclic ring system may be substituted by one or more groups selected from carbonyl, C$_{1-4}$alkyl, C$_{2-4}$alkenyl, C$_{2-4}$alkynyl, halo, hydroxy, C$_{1-4}$alkoxy, carboxy or C$_{2-4}$alkoxycarbonyl. Examples of such azabicyclic ring systems include:

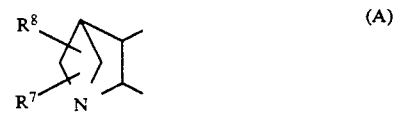

(A)

-continued (B)

[Structure B: bicyclic amine with R⁶ and R⁷ substituents]

(C)

[Structure C: bicyclic amine with R⁶ and R⁷ substituents]

(D)

[Structure D: bicyclic amine with R⁷ and R⁸ substituents]

(E)

[Structure E: bicyclic amine with R⁷ and R⁸ substituents]

(F)

[Structure F: bicyclic amine with R⁷ and R⁸ substituents]

wherein $R^6$ and $R^7$ independently represent H, $C_{1-4}$ alkyl, $C_{2-4}$ alkenyl, $C_{2-4}$ alkynyl, halo, hydroxy, $C_{1-4}$ alkoxy, carboxy or ($C_{1-4}$ alkoxy)carbonyl; or $R^6$ and $R^7$ together represent carbonyl.

It will be appreciated that the nitrogen atom in the azabicyclic ring system will carry a lone pair of electrons.

It will also be appreciated that the $R^6$ and $R^7$ substituents may be present at any position in the azabicyclic ring system, including, where appropriate, the bridgehead carbon atom depicted in structures A to F above.

Suitably the group $R^6$ is H or methyl; and $R^7$ is H, $C_{1-4}$ alkyl, hydroxy or $C_{1-4}$ alkoxy, preferably H, methyl, hydroxy or methoxy. Preferably one or, more preferably, both of $R^6$ and $R^7$ is H.

Suitably the azabicyclic ring system of which Q is the residue is a 1-azabicyclo [2.2.1]heptanyl (1-azanorbornanyl), 1-azabicyclo[2.2.1]octanyl (quinuclidinyl) or 1-azabicyclo[3.2.1]octanyl ring system of formula (B), (C) or (D) above respectively, any of which is optionally substituted by methyl or hydroxy. A preferred ring system is 1-azabicyclo[2.2.2.]octane (quinuclidine) of formula (C) above.

The alkyl, alkenyl and alkynyl groups referred to with respect to any of the above formulae may represent straight, branched or cyclic groups. Thus, for example, suitable alkyl groups include methyl, ethyl, n- or isopropyl, n-, sec-, iso- or tert-butyl, cyclopropyl, cyclobutyl, cyclopentyl or cyclohexyl, and cycloalkylalkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

Preferably, the double bond is present.

Where X is halo, preferably this is fluoro.

In one subgroup of compounds according to the invention, X is H, —OH or =O, preferably —OH.

In a further subgroup of compounds of formula (I), X is halo, preferably fluoro.

Preferably X is OH or halo, more preferably X is fluoro.

When $R^1$ is H, $R^2$ suitably represents phenyl or thienyl, which groups may be optionally substituted by halo or trifluoromethyl, and X suitably represents H, —OH or =O.

When $R^1$ is other than H, preferably $R^1$ and $R^2$ are identical.

In a particular embodiment, $R^1$ and $R^2$ each represents unsubstituted phenyl.

Preferably $R^1$ is H or unsubstituted phenyl.

Preferably $R^2$ is unsubstituted phenyl.

Suitable values for the groups $R^3$, $R^4$ and $R^5$ include H, $C_{1-6}$ alkyl, $C_{2-6}$ alkenyl, $C_{2-6}$ alkynyl, halo, cyano, nitro, trifluoromethyl, —$OR^a$, $SCH_3$, $SOCH_3$, $SO_2CH_3$, —$NR^aR^b$, —$NR^aCOR^b$, —$NR^aCO_2R^b$, —$CO_2R^a$ and —$CONR^aR^b$, where $R^a$ and $R^b$ are as previously defined, such as H, straight or branched $C_{1-6}$ alkyl, $C_{1-6}$ alkoxy, nitro, trifluoromethyl and halo, especially chloro or fluoro. Preferably one or two of $R^3$, $R^4$ and $R^5$ are selected from H, straight or branched $C_{1-4}$ alkyl, straight or branched $C_{1-4}$ alkoxy, trifluoromethyl or halo, especially fluoro. Especially preferred is where they are independently selected from H, methyl, methoxy, trifluoromethyl or fluoro. When the phenyl ring is disubstituted, the substituents are preferably in the 3- and 5-positions of the ring such as 3,5-dimethyl or, more preferably, 3,5-bistrifluoromethyl. Preferably, at least one of $R^3$, $R^4$ and $R^5$ is other than H. More preferably two of $R^3$, $R^4$ and $R^5$ are other than H. Especially preferred are compounds wherein two of $R^3$, $R^4$ and $R^5$ are trifluoromethyl.

The compounds according to the invention may exist both as enantiomers and as diastereomers. In particular, the relative orientation of the 2- and 3- substituents in formula (I) where the double bond is absent may give rise to cis and trans diastereoisomers of which the trans stereochemistry is preferred. It is to be understood that all such isomers and mixtures thereof are encompassed within the scope of the present invention.

A particular sub-class of compounds according to the invention is represented by the compounds of formula (IIA) and salts and prodrugs thereof:

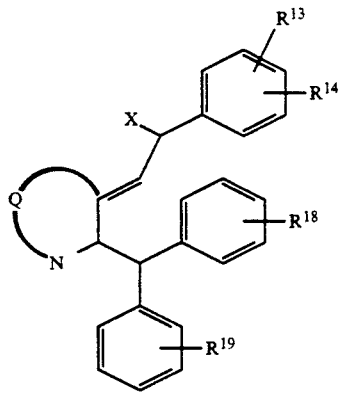

wherein

X represents H, —OH, =O or halo;

$R^{13}$ and $R^{14}$ independently represent H, $C_{1-6}$ alkyl, halo, cyano, nitro, trifluoromethyl, hydroxy, $C_{1-6}$ alkoxy or amino; and $R^{18}$ and $R^{19}$ independently represent H, halo or trifluoromethyl.

Particular values of $R^{13}$ and $R^{14}$ include H, $C_{1-4}$ alkyl especially methyl, $C_{1-4}$ alkoxy especially methoxy, halo, especially chloro and fluoro, nitro and trifluoromethyl. Preferably, at least one of $R^{13}$ and $R^{14}$ is other than H. More preferably each of $R^{13}$ and $R^{14}$ represents H or a methyl, methoxy, fluoro or a trifluoromethyl group.

In one subgroup of compounds of formula (IIA), X is H, —OH or —O, preferably —OH.

In a further subgroup of compounds of formula (IIA), X is halo, preferably fluoro.

Preferably, $R^{18}$ and $R^{19}$ both represent H.

A further sub-class of compounds according to the invention is represented by the compounds of formula (IIB), and salts and prodrugs thereof:

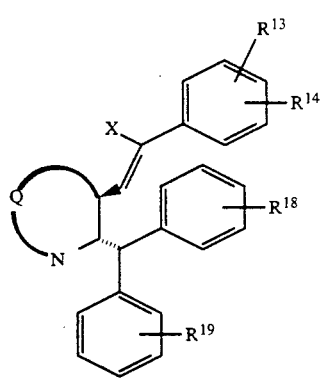

wherein X, $R^{13}$, $R^{14}$, $R^{18}$ and $R^{19}$ are as defined for formula (IIA) above.

In one subgroup of compounds of formula (IIB), X is H, —OH or —O, preferably —OH.

In a further subgroup of compounds of formula (IIB), X is halo, preferably fluoro.

A further sub-class of compounds according to the invention is represented by the compounds of formula (IIC) and salts and prodrugs thereof:

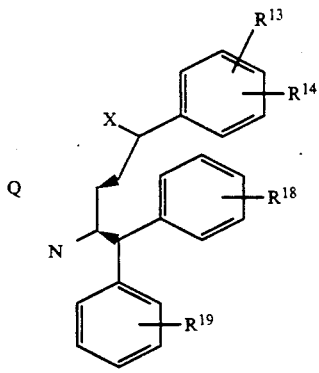

wherein X, $R^{13}$, $R^{14}$, $R^{18}$ and $R^{19}$ are as defined for formula (IIA) above.

A further sub-class of compounds according to the invention is represented by the compounds of formula (IID) and salts and prodrugs thereof:

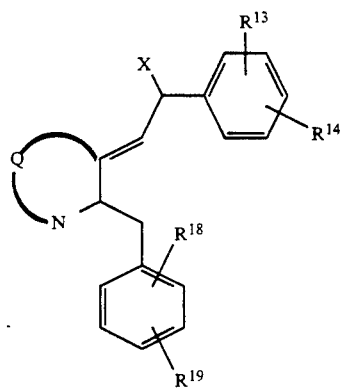

and X, $R^{13}$, $R^{14}$, $R^{18}$ and $R^{19}$ are as defined for formula (IIA) above.

In one subgroup of compounds of formula (IIB), X is H, —OH or —O, preferably —OH.

In a further subgroup of compounds of formula (IIB), X is halo, preferably fluoro.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, oxalic acid, fumaric acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula I which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The compounds of the present invention are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as AIDS related dementia, senile dementia of the Alzheimer type, Alzheimer's disease and Down's syndrome; demyelinating diseases such as MS and ALS and other neuropathological disorders such as diabetic or peripheral neuropathy, AIDS related neuropathy, chemotherapy-induced neuropathy, and neuralgia; respiratory diseases such as chronic obstructive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine. Thus, the present invention further provides a compound for use in the manufacture of a medicament for the treatment of physiological disorders associated with an excess of tachykinins, especially substance P. The present invention also provides a method for the treatment or prevention of physiological disorders associated with an excess of tachykinins, especially substance P, which method comprises administration to a patient in need thereof of a tachykinin reducing amount of a compound or composition of this invention.

In the treatment of conditions involving actions of tachykinins released physiologically in response to noxious or other stimuli, a suitable dosage level is about 0.001 to 50 mg/kg per day, such as 0.001 to 25 mg/kg per day, preferably about 0.005 to 10 mg/kg per day, and especially about 0.05 to 5 mg/kg per day. The compounds may be administered on a regimen of 1 to 4 times per day.

The compounds according to the invention wherein X is OH may be prepared by a process (A) which comprises reacting a compound of formula (III) with a compound of formula (IV):

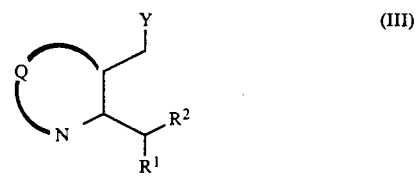

(III)

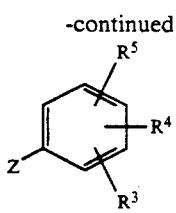

wherein Q, $R^1$, $R^2$, $R^3$, $R^4$ and $R^5$ are as defined in formula (I); Y represents CHO (intermediates (IIIB)); and Z is a metal, such as aluminium or lithium, or metal halide.

The group Z in the reaction of (III) with (IV) suitably represents a metal such as aluminium or, preferably, the residue of a Grignard agent such as MgBr. The reaction is preferably carried out in an inert organic solvent such as an ether such as diethyl ether, tetrahydrofuran or a mixture thereof.

The compounds according to the invention wherein the double bond is present and X is =O may be prepared by a process (B) which comprises hydrolysing a compound of formula (V):

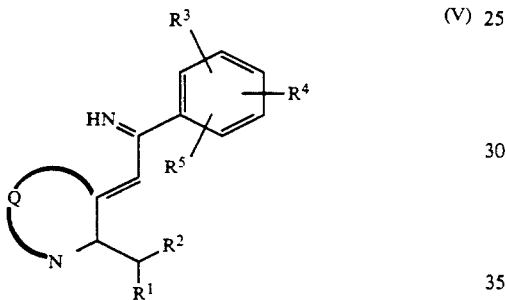

wherein Q, $R^1$, $R^2$, $R^3$, $R^4$ and $R^5$ are as defined in formula (I). The reaction may take place with dilute acid such as dilute mineral acid, for example, hydrochloric acid.

The compound of formula (V) need not be isolated but may be hydrolized in situ after being prepared from the corresponding compound of formula (IIIA) wherein Y represents CN by reaction with the corresponding compound of formula (IV) (wherein Z is preferably lithium) as described above in relation to preparing compounds of formula (I) wherein the double bond is present and X is OH.

The compounds prepared according to processes (A) and (B) above may be converted to other compounds of formula (I). Thus, for example, the compounds according to the invention wherein the double bond is absent and X is =O may be prepared from the corresponding compounds of formula (I) wherein X is OH, by oxidation. The oxidation may be effected by standard methods known to those skilled in the art, for example, using pyridine-dichromate or pyridinium chlorochromate.

The compounds according to the invention wherein X is H may be prepared by reducing the corresponding compound of formula (I) wherein X is OH. The reduction may be effected by standard methods known to those skilled in the art such as catalytic reduction by hydrogen in the presence of a catalyst such as platinum or palladium, preferably palladium dihydroxide. Such reduction is preferably carried out in the presence of a polar solvent such as an alcohol such as ethanol or an acid such as an inorganic acid, for example, hydrochloric acid, or a mixture thereof. Alternatively, the reduction may be carried out by, for example, lithium aluminium hydride/aluminium trichloride in the presence of a solvent such as an ether such as diethyl ether or tetrahydrofuran or a mixture thereof, preferably at ambient temperature such as around 25° C.

The compounds according to the invention wherein X is halo may be prepared from the corresponding compounds of formula (I) wherein X is OH using conventional techniques, for example, by reaction with a suitable halogenating agent. Examples of halogenating agents include thionyl halides, phosphorous trihalides and phosphorous pentahalides.

A preferred halogenating agent for use in the reaction is diethylaminosulphurtrifluoride. The reaction is preferably conducted at low temperature, for example, at about −15° to +5° C.

The compounds of formula (IIIA) wherein the double bond is present and Y represents CN may be prepared by reaction of a compound of formula (VI) with a Wittig reagent:

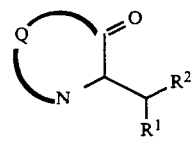

wherein Q, $R^1$ and $R^2$ are as defined in formula (I). Preferably, the compound of formula (VI) is reacted with a reagent of formula $(alkoxy)_2PO(CH_2CN)$, such as $(EtO)_2PO(CH_2CN)$ or $(iPrO)_2PO(CH_2CN)$ in the presence of an alkali or alkaline earth metal salt of an alcohol such as potassium t-butoxide in an inert organic solvent such as toluene at an elevated temperature in the range of from 25° C. to 50° C., preferably around 50° C.

The compounds of formula (IIIA) wherein the double bond is absent and Y represents CN may be prepared from the corresponding compounds of formula (IIIA) wherein the double is present, by reduction. Suitable procedures and reagents will be readily apparent to one skilled in the art, and include dissolving metal reduction, for example, using magnesium in methanol.

The intermediates of formula (IIIB) above wherein Y is CHO may be prepared by the procedures described in J. Med. Chem., 1974, 17, 497, and J. Med. Chem., 1975, 18, 587; or by methods analogous thereto. For example, from the corresponding intermediate of formula (IIIA) wherein Y represents CN for example with a standard agent such as DIBAL-H (available from Aldrich).

Where they are not commercially available, the intermediates of formula (IV) above may be prepared by the procedures described in the accompanying Examples or by alternative procedures which will be readily apparent to one skilled in the art.

Where the above-described process for the preparation of the compounds according to the invention gives rise to mixtures of stereoisomers these isomers may be separated, suitably by conventional techniques such as preparative chromatography.

The novel compounds may be prepared either by enantiospecific synthesis or by resolution. The novel compounds may, for example, be prepared by resolution using standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following Examples illustrate the preparation of compounds according to the invention.

DESCRIPTION 1

E-3-[Methylenecyano]-2-benzhydryl quinuclidine (hereafter called Intermediate 1)

Potassium t-butoxide (11.5 g) was added to a one neck round bottom flask under nitrogen. To this was added 200 ml of dry toluene and the mixture is cooled to 0° C. The slow addition of diisopropyl cyanomethyl phosphonate (20 ml, 0.103 moles) took place after which the reaction mixture was allowed to warm to room temperature and stirred for 60 min. The reaction mixture was re-cooled to 0° C. for the addition of 2-diphenylmethyl quinuclidin-3-one (10 g) [prepared according to the procedure described by E. J. Warawa, Vol. 18, No. 6, pg 587, 1975]. The mixture was heated at 50° C. for 16 h. The reaction was quenched with water and extracted into ethyl acetate. The organic layer was separated, dried ($Na_2SO_4$), filtered and concentrated in vacuo to give the crude product. The product was purified by crystallisation from ethyl acetate/petrol as a white solid. $^1$H NMR ($CDCl_3$) 1.66-1.90 (4H, m), 2.48-2.64 (1H, m), 2.70-3.14 (4H, m), 3.93-3.94 (1H, m), 4.00-4.04 (1H, d), 4.22-4.26 (1H, d), 7.10-7.36 (10H, m).

DESCRIPTION 2

E-3-[Methylenecarboxaldehyde]-2-benzhydryl quinuclidine (hereafter called Intermediate 2)

Intermediate 1 (5.0 g) was added to a one neck round bottom flask under nitrogen. To this is added 100 ml of dry dichloromethane and the flask is cooled to −78° C. in a dry ice/acetone bath. DIBAL-H-1.2M solution in toluene-(33 ml) is added dropwise to this mixture which is then stirred for a further 90 min at −78° C. After warming to 0° C., 1M hydrochloric acid (40 ml) was added to the reaction mixture which was then basified to pH 10 with solid sodium hydroxide and extracted with ethyl acetate. The organic layer is separated, dried ($Na_2SO_4$), filtered and concentrated in vacuo to give the crude product. Purification is by crystallisation from ethyl acetate/hexane to give a white solid. $^1$H NMR ($CDCl_3$) 1.66-1.98 (4H, m), 2.50-2.66 (1H, m), 2.78-3.14 (3H, m), 3.52-3.62 (1H, m), 4.10-4.14 (1H, d), 4.22-4.26 (1H, d), 4.76-4.82 (1H, dd), 7.10-7.40 (10H, m), 9.76-9.80 (1H, d).

EXAMPLE 1

E-3-[Methylene(2-methoxyphenyl)hydroxymethyl]-2-benzhydryl)quinuclidine

Magnesium turnings (230 mg) are placed in a three neck round bottom flask fitted with a reflux condenser, under an atmosphere of nitrogen. 20 ml of dry tetrahydrofuran or dry diethyl ether was added to this followed by the dropwise addition of the bromoanisole (1.2 ml). Vigorous stirring for 5 min initiated the Grignard reaction as shown by refluxing THF. The reaction mixture was then allowed to stir at room temperature for 30 min after which time the Grignard reagent had formed completely as shown by the total disappearance of the magnesium. In a separate one neck flask under nitrogen, Intermediate 2 (1.0 g) was dissolved in 10 ml of dry tetrahydrofuran and cooled to −78° C. in a dry ice/acetone bath. The Grignard solution was then added dropwise via syringe over a period of 5 min. The reaction mixture was then stirred at this temperature for a further 10 min before being allowed to warm to 0° C. over 15 min. The reaction was quenched by the addition of saturated ammonium (50 ml) and extracted into ethyl acetate. The organic layer was separated, dried ($Na_2CO_3$), filtered and concentrated in vacuo to give the crude products. Purification was by flash chromatography on silica (ethyl acetate, 10% methanol/ethyl acetate). Isomer A. White solid. $^1$H NMR ($CDCl_3$) 1.46-1.56 (1H, m), 1.58-1.76 (2H, m), 1.82-1.92 (1H, m), 2.47-2.56 (1H, m), 2.66-2.74 (1H, m), 2.95-3.03 (3H, m), 3.71 (3H, s), 4.03-4.07 (1H, d), 4.12-4.16 (1H, d), 4.26-4.31 (1H, d), 5.41-5.43 (1H, d), 6.77-6.83 (1H, d), 6.85-6.87 (1H, tr), 6.99-7.02 (1H, d), 7.12-7.36 (11H, m). Isomer B. White solid. M.Pt. 155°-156° C. $^1$H NMR ($CDCl_3$) 1.67-1.77 (4H, m), 2.46-2.55 (2H, m), 2.84-3.08 (3H, m), 3.80 (3H, s), 3.98-4.01 (1H, d), 4.17-4.22 (1H, d), 4.43-4.45 (1H, d), 5.48-5.51 (1H, d), 6.82-7.60 (14H, m).

EXAMPLE 2

E-[3-[Methylene(4-fluorophenyl)hydroxymethyl]-2-benzhydryl)quinuclidine

Intermediate 2 (0.75 g) was placed in a one neck round bottom flask under nitrogen. To this was added 50 ml of dry tetrahydrofuran. This solution is cooled to −78° C. in a dry ice/acetone bath before the dropwise addition of commercially available p-fluorophenyl magnesium bromide [2.0M solution in diethyl ether, (2.6 ml)]. The mixture was allowed to warm to room temperature and stirred for 15 min. The reaction was quenched by the addition of saturated ammonium chloride solution (30 ml) and extracted into ethyl acetate. The organic layer was separated, dried ($Na_2SO_4$), filtered and concentrated in vacuo to give the crude products. T.l.c. silica 20% methanol/ethyl acetate Isomer A $R_f$=0.34, Isomer B $R_f$=0.24. Purification was by flash chromatography on silica (10-20% methanol/ethyl acetate). Isomer B crystallised from diethyl ether/hexane. White solid. M.Pt. 127°-129° C. $^1$H NMR ($CDCl_3$) 1.66-1.77 (4H, m), 2.47-2.56 (1H, m), 2.83-3.10 (4H, m), 3.97-4.00 (1H, d), 4.18-4.21 (1H, d), 4.37-4.40 (1H, d), 5.27-5.30 (1H, d), 6.92-7.34 (14H, m). Isomer A. $^1$H NMR ($CDCl_3$) 1.48-1.90 (4H, m), 2.51-2.60 (1H, m), 2.67-2.77 (1H, m), 2.94-3.07 (3H, m), 4.04-4.15 (3H, 3 x d), 5.20-5.22 (1H, d), 6.91-7.39 (14H, m).

Oxalate salt of isomer B was made by adding a solution of the free base in anhydrous methanol to a solution of oxalic acid (1.5 equivalents) in ether. The resulting white precipitate was filtered and dried. White solid. M.Pt. 163°–165° C. $^1$H NMR (D$_6$-DMSO) 1.52–1.64 (1H, m), 1.76–1.90 (2H, m), 2.00–2.12 (1H, m), 2.78–2.90 (1H, m), 3.04–3.26 (4H, m), 4.34–4.37 (1H, d), 4.53–4.55 (1H, d), 4.90–4.93 (1H, d), 5.14–5.16 (1H, d), 6.97–7.56 (14H, m).

EXAMPLE 3

E-3-[Methylene(3-trifluoromethylphenyl)hydroxymethyl]-2-benzyhydryl quinuclidine The procedure of Example 1 was followed, using 0.70 g of Intermediate 2; 0.92 ml of 3-bromobenzotrifluoromethane; and 0.16 g of magnesium turnings. T.l.c. silica 20% methanol/ethyl acetate. Isomer A R$_f$=0.40. Isomer B R$_f$=0.27. Purification is by flash chromatography on silica. Eluant 5% methanol/ethyl acetate. Products crystallised from diethyl ether/hexane. Isomer A: white solid, M.Pt. 145°–147° C. $^1$H NMR (CDCl$_3$) 1.50–1.94 (4H, m), 2.54–2.84 (2H, m), 2.96–3.16 (3H, m), 4.06–4.18 (3H, m), 5.26–5.27 (1H, d), 7.14–7.48 (14H, m). Isomer B: white solid, M.Pt. 108°–110° C. $^1$H NMR (CDCl$_3$) 1.72–1.90 (4H, m), 2.50–2.64 (1H, m), 2.84–3.18 (4H, m), 3.99–4.02 (1H, d), 4.21–4.24 (1H, d), 4.26–4.27 (1H, d), 5.36–5.37 (1H, d), 6.69–7.52 (14H, m).

EXAMPLE 4

E-3-[Methylene(hydroxymethyl)phenyl]-2-benzhydryl quinuclidine

The procedure of Example 2 was followed, using 1.0 g of Intermediate 2 and 2.3 ml of commercially available phenylmagnesium bromide (3.0M solution in ether). T.l.c silica 20% methanol/ethyl acetate. Isomer A R$_f$=0.27. Isomer B R$_f$=0.18. Purification is by flash chromatography on silica. Eluant 5–20% methanol/ethyl acetate.

Isomer B crystallised from diethyl ether/hexane. White solid, M.Pt. 146°–148° C. $^1$H NMR (CDCl$_3$) 1.64–1.80 (4H, m), 2.42–2.58 (1H, m), 2.78–3.12 (3H, m), 3.96–4.00 (1H, d), 4.16–4.20 (1H, d), 4.38–4.44 (1H, dd), 5.28–5.32 (1H, d), 6.90–7.36 (15H, m). Isomer A. $^1$H NMR (CDCl$_3$) 1.44–1.94 (4H, m), 2.46–2.78 (2H, m), 2.90–3.10 (3H, m), 4.02–4.18 (3H, m), 5.20–5.24 (1H, d), 7.06–7.42 (15H, m). Oxalate salt of isomer B was made by adding a solution of the free base in anhydrous methanol to a solution of oxalic acid (1.5 equivalents) in ether. The resulting white precipitate was filtered and dried. White solid, M.Pt. 158°–159° C. $^1$H NMR (D$_6$-DMSO) 1.52–1.64 (1H, m), 1.84–2.00 (2H, m), 2.16–2.28 (1H, m), 2.96–3.08 (1H, m), 3.08–3.20 (1H, m), 3.22–3.40 (3H, m), 4.42–4.46 (2H, s x d), 5.15–5.18 (1H, d), 5.20–5.30 (1H, d), 7.06–7.66 (15H, m).

EXAMPLE 5

E-3-[Methylenebenzyl]-2-benzhydryl quinuclidine

A mixture of diastereomers of E-3-[methylene-2-hydroxymethylphenyl]-2-benzhydryl quinuclidine (Example 4) (0.45 g) were suspended in ethanol (20 ml) and 1M hydrochloric acid was added until the compound had completely dissolved. Palladium hydroxide on charcoal (20 mg) was added and the mixture hydrogenated at 50 psi for 16 h. The catalyst was filtered off and the crude product concentrated in vacuo, diluted with water, basified to pH 10 with 1M sodium hydroxide solution and extracted into ethyl acetate. The organic layer is separated, dried (Na$_2$SO$_4$), filtered and concentrated in vacuo. The oxalate salt was made by adding a solution of the free base in anhydrous methanol to a solution of oxalic acid (1.5 equivalents) in ether. The resulting precipitate was filtered and dried. White solid. $^1$H NMR (CD$_3$OD) 1.86–1.98 (1H, m), 2.02–2.18 (2H, m), 2.22–2.36 (1H, m), 3.08–3.62 (5H, m), 4.37–4.41 (1H, d), 4.60–4.64 (1H, tr), 5.17–5.21 (1H, d), 6.27–7.65 (15H, m).

EXAMPLE 6

E-3-[Methylene(3-trifluoromethyl)benzyl]-2-benzhydryl quinuclidine

The procedure of Example 5 was followed, but using E-3-[methylene-2-(3-trifluoromethylphenyl)hydroxymethyl]-2-benzhydryl quinuclidine (Example 3) (0.15 g) and Pd(OH)$_2$ (20 mg) on charcoal. The mixture was hydrogenated at 50 psi for 3 hours. The crude product was purified by flash chromatography on silica (0–10% methanol/ethyl acetate). White solid. $^1$H NMR (CDCl$_3$) 1.56–1.90 (4H, m), 2.26–3.14 (7H, m), 4.04–4.10 (1H, d), 4.18–4.26 (2H, d and tr), 6.94–7.46 (4H, m). The oxalate salt was made by adding a solution of the free base in anhydrous methanol to a solution of oxalic acid (1.5 equivalents) in ether. The resulting precipitate was filtered and dried. White solid. M.Pt 88°–90° C. $^1$H NMR (D$_6$-DMSO) 1.72–1.84 (1H, m), 1.88–2.04 (2H, m), 2.06–2.20 (1H, m), 2.90–3.04 (1H, m), 3.12–3.40 (6H, m), 4.39–4.42 (1H, d), 4.43–4.48 (1H, tr), 5.13–5.16 (1H, d), 7.06–7.66 (14H, m).

EXAMPLE 7

E-3-[Methylene(3,5-bistrifluoromethylphenyl)oxo]-2-benzhydryl quinuclidine 3,5-bis(trifluoromethyl)bromobenzene (1.2 ml) was added to a one neck round bottom flask under nitrogen. To this was added 15 ml of dry ether and the mixture cooled to 0° C. n-Butyllithium 2.5M solution in ether/hexane (2.8 ml) was added dropwise to the mixture which was then stirred at 0° C. for a further 60 mins. Meanwhile, Intermediate 1 (1.0 g) was added to a separate one neck round bottom flask also under nitrogen. To this was added 20 ml of dry tetrahydrofuran and the resulting solution cooled to 0° C. The solution of Intermediate 1 was then slowly added resulting in a dark brown solution which is stirred at 0° C. for a further 15 mins. 1M hydrochloric acid (30 ml) was added to the mixture which was allowed to warm to room temperature and stirred for 90 mins. Work up consisted of recooling to 0° C., adding 5.0M sodium hydroxide until pH 10 and extracting with ethyl acetate. The organic layer was separated, dried (Na$_2$SO$_4$), filtered and concentrated in vacuo to give the crude product. T.l.c. silica 30% ethyl acetate/petrol. R$_f$=0.36. Purification is by flash chromatography on silica 10–40% ethyl acetate/petrol. The product is recrystallised from methanol. Yellow solid, M.Pt. 176°–177° C. $^1$H NMR (CDCl$_3$) 1.70–1.98 (4H, m), 2.56–2.68 (1H, m), 2.76–2.86 (1H, m), 3.02–3.14 (2H, m), 3.98–4.04 (1H, m), 4.18–4.21 (1H, d), 4.28–4.31 (1H, d), 5.76 (1H, s), 7.16–7.42 (10H, m), 7.76 (2H, s), 7.94 (1H, s).

EXAMPLE 8

E-3-[Methyleneketophenyl]-2-benzhydrylquinuclidine

Intermediate 1 (1.0 g) was added to a one neck round bottom flask under nitrogen and dissolved in 25 ml of dry tetrahydrofuran. This solution was cooled to 0° C. for the dropwise addition of phenyllithium 1.8M solution in cyclohexane/ether (4.4 ml). The reaction mixture was stirred at 0° C. for a further 15 mins. 1M hydrochloric acid (30 ml) was added to the mixture which was allowed to warm to room temperature and stirred for 2 h. Work up consisted of re-cooling to 0° C., basifying with 5.0M sodium hydroxide solution and extracting with ethyl acetate. The organic layer was separated, dried (Na$_2$SO$_4$), filtered and concentrated in vacuo to give the crude product as a yellow oil. T.l.c. Silica 30% ethyl acetate/petrol. R$_f$=0.14. Product R$_f$=0.14. The product was purified by crystallisation from ether. Pale yellow solid. $^1$H NMR (CDCl$_3$) 1.60–1.90 (4H, m), 2.52–2.68 (1H, m), 2.74–2.90 (1H, m), 2.98–3.16 (2H, m), 3.80–3.88 (1H, m), 4.18–4.22 (1H, d), 4.28–4.32 (1H, d), 5.86 (1H, s), 7.12–7.46 (15H, m). The oxalate salt was made by adding a solution of the free base in anhydrous methanol to a solution of oxalic acid (1.5 equivalents) in ether. The resulting precipitate was filtered and dried. White solid, M.Pt. 175°–178° C. $^1$H NMR (D$_6$-DMSO) 1.84–2.00 (2H, m), 2.00–2.24 (2H, m), 2.98–3.10 (1H, m), 3.12–3.26 (1H, m), 3.26–3.42 (2H, m), 3.78–3.84 (1H, m), 4.58–4.82 (1H, d), 5.34–5.46 (1H, d), 5.92 (1H, s), 7.11–7.75 (15H, m).

EXAMPLE 9

E-3-[Methylene-2-(3,5-bistrifluoromethyl)hydroxymethyl]-2-benzhydrylquinuclidine The procedure of Example 1 was followed, but using 1.0 g of Intermediate 2, 1.36 ml of 3,5-bis(trifluoromethyl)bromobenzene. Purification by flash chromatography on silica 50% ethyl acetate/hexane-35% methanol/ethyl acetate. Isomer A crystallised from ether/hexane. White solid, M.Pt. 174° C. $^1$H NMR (CDCl$_3$) 1.36–1.50 (1H, m), 1.52–1.80 (3H, m), 2.32–2.46 (1H, m), 2.56–2.70 (1H, m), 2.76–2.98 (3H, m), 3.94–3.98 (1H, d), 4.00 (2H, s), 5.06–5.10 (1H, d), 7.00–7.30 (10H, m), 7.42 (2H, s), 7.60 (1H, s). Isomer B $^1$H NMR (CDCl$_3$) 1.8 (4H, m), 2.5–3.2 (5H, m), 4.0 (1H, d), 4.15 (1H, d), 4.23 (1H, d), 5.4 (1H, dd), 6.7–7.7 (13H, m).

EXAMPLE 10

E-3-[Methylene-2-(3,5-bistrifluoromethyl)fluoromethyl]-2-benzhydrylquinuclidine (Isomer A) oxalate salt The product of Example 9 (Isomer A) (0.30 g) was dissolved in dichloromethane and the solution cooled to −10° C. Diethylaminosulphurtrifluoride (0.11 ml) was added and the reaction mixture stirred for 0.5 h. After quenching by the addition of saturated sodium bicarbonate solution and extracting with dichloromethane, the organic layer was dried (Na$_2$CO$_3$) and concentrated to give an oil. The oil was purified by chromatography on silica eluting with 20% ethyl acetate/petroleum ether-30% ethyl acetate/petroleum ether. The product was dissolved in methanol and added to an ethereal solution of oxalic acid. The precipitated salt was isolated by filtration to give a white solid, mp 105°–107° C.

EXAMPLE 11

E-3-[Methylene-2-(3,5-bistrifluoromethyl)fluoromethyl]-2-benzhydrylquinuclidine (Isomer B)

The title compound was prepared from the product of Example 9 (Isomer B) analogously to the preparation of the product of Example 10 (free base); mp 190° C.; $^1$H NMR (CDCl$_3$) 1.5–1.9 (1H, m), 2.5–3.1 (6H, m), 4.1 (1H, m), 4.26 (1H, dd), 5.96 (1H, dd), 7.1–7.4 (10H, m), 7.32 (2H, s), 7.77 (1H, s).

EXAMPLE 12

E-3-[Methylene-2-keto(3,5-dimethyl)phenyl]-2-benzhydryl quinuclidine n-Butyllithium (2.8 ml) was added dropwise at −78° C. to a solution of 5-bromo-m-xylene (0.95 ml) in 30 ml anhydrous tetrahydrofuran under nitrogen. The reaction mixture was then warmed to 0° C. and stirred for a further 10 min. Intermediate I as a solution in 20 ml anhydrous tetrahydrofuran was then added dropwise resulting in an orange-red solution. After stirring for 15 min the reaction was quenched with 20 ml 1M hydrochloric acid and the bright yellow solution allowed to warm to room temperature and stirred for 2 h. Solid potassium hydroxide was added till pH 11 and the aqueous layer extracted with ethyl acetate. The organic layer was dried (MgSO$_4$), filtered and solvent removed in vacuo. The product precipitated out when methanol was added to the residue and the resulting solid was recrystallized from dichloromethane/methanol. Pale yellow solid. M.P. 205°–206° C. $^1$H NMR (CDCl$_3$, 250 MHz) 1.76 (4H, m, quinuclidine-H), 2.56 (1H, m, quinuclidine-H), 2.84 (1H, m, quinuclidine-H), 3.03 (2H, m, N—CH$_2$), 3.09 (1H, s, bridgehead (quinucl.)), 4.20 (1H, d, J=12 Hz, PhCHPh), 4.30 (1H, d, J=12 Hz, N-C$\underline{H}$), 5.86 (1H, s, vinyli$\overline{c}$), 6.95 (2H, s, Aromatic-H), 7.08 (1$\overline{H}$, s, Aromatic-H), 7.14–7.41 (10H, m, Aromatic-H); MS (m/z, %): (421 (M$^+$), 40%); CHN, calc for: C, 85.57%; H, 7.45%; N, 3.28%: Found: C, 84.85%, H, 7.48%; N, 3.39%.

EXAMPLE 13

E-[3-Methylene(3,5-dimethylphenyl)hydroxymethyl]-2-benzhydryl quinuclidine

Compound prepared according to the method described in Example 1 using 5-bromo-m-xylene to generate the Grinard reagent. Column chromatography on silica eluting with ethyl acetate furnished the title compound. White solid, Diastereomer A. $^1$H NMR (360 MHz, CDCl$_3$) 1.55 (1H, m, quinuclidine-H), 1.71 (2H, m, quinuclidine-H), 1.86 (1H, m, quinuclidine-H), 2.25 (6H, s, 2 x CH$_3$), 2.58 (1H, m, N—CH$_2$), 2.75 (1H, m, N—CH$_2$), 3.03 (3H, m, N—CH$_2$, quinuclidine-bridgehead), 4.07 (1H, d, J=11.5 Hz, PhCHPh), 4.14 (1H, d, J=11.5 Hz, NCH), 4.15 (1H, d, J=8.$\overline{0}$ Hz, vinylic), 5.16 (1H, d, J=8.0 Hz, CH—OH), 6.69 (2H, s, Ar—H), 6.63 (1H, s, Ar—H), 7.2$\overline{3}$ (8H, m, Ar—H), 7.38 (2H, d, Ar—H). MS (m/z, %): (423 (M$^+$), 30%), (405 (M$^+$−18), 25%). CHN: calc. for C, 84.72; H, 7.95; N, 3.25: Found: C, 84.54; H, 7.93; N, 3.28.

EXAMPLE 14

E[3-Methylene(2,6-dimethylphenyl)hydroxymethyl]-2-benzhydryl quinuclidine

*Compound prepared according to method described in Example 1 using 2-bromo-m-xylene to generate the Grinard reagent. Column chromatography on silica eluting with ethyl acetate gave the title compound. White solid. M.P. 168°–168° C. Diastereomer A. $^1$H NMR (360 MHz, CDCl$_3$) 1.31 (1H, m, quinuclidine-H), 1.59 (2H, m, quinuclidine-H), 1.80 (1H, m, quinuclidine-H), 2.04 (6H, s, 2×CH$_3$), 2.29 (1H, m, quinuclidine-bridgehead), 2.71–2.81 (4H, m, N—CH$_2$), 4.13 (1H, d, PhCHPh), 4.24 (1H, d, NCH), 4.60 (1H, d, J=3.6 Hz, vinyl$\overline{ic}$), 4.74 (1H, d, J=7.2 Hz, CH—O$\underline{H}$), 5.50 (1H, dd, J=3.6 Hz, 7.2 Hz, C$\underline{H}$OH), 6.81 (2$\overline{H}$, d, Ar—H), 6.89 (1H, dd, Ar—H), 7.02 (1H, dd, Ar—H), 7.09 (1H, dd, Ar—H), 7.15 (4H, m, Ar—H), 7.41 (4H, m, Ar—H). MS (m/z, %): (423 (M+), 20%), (405 (M+ −18), 25%). CHN: calc for C, 84.21%; H, 8.09%; N, 3.17%: found: C, 84.52%; H, 8.44%; N, 3.18%.

EXAMPLE 15

E-3-[Methylene-(3,5-bistrifluoromethylphenyl)hydroxymethyl]-2-benzyl quinuclidine a) 2-Benzylidene quinuclidine-3-one

To quinuclidine-3-one hydrochloride (Aldrich Chemical Co.) (49.9 g) in water (200 ml) was added sodium hydroxide (12.5 g, 0.310 mol). The aqueous layer was extracted with dichloromethane (2×200 ml) and the combined organic layers dired ($Na_2CO_3$), filtered, and evaporated in vacuo to give a colourless oil. The oil (38.64 g) was dissolved in ethanol (400 ml) and sodium hydroxide (3 g) added, followed by benzaldehyde (32.8 g). The reaction mixture was heated at reflux for 2 h. On cooling the product crystallized from the solution as a yellow solid. $^1H$ NMR ($CDCl_3$) δ 1.96-2.08 (4H, m), 2.62-2.66 (1H, m), 2.92-3.24 (4H, m), 7.02 (1H, s), 7.32-7.42 (3H, m), 8.00-8.04 (2H, m).

b) 2-Benzyl quinuclidine-3-one

To a solution of the product of part a) (3 g) in ethyl acetate was added palladium on carbon (0.3 g) and the reaction mixture shaken under a hydrogen atmosphere at 30 psi for 4 hours. The catalyst was then filtered off and the solvent removed in vacuo. Purification by flash chromatography on silica eluting with 50-100% ethyl acetate/petroleum ether gave the title compound as a white solid; $R_f$=0.36 (ethyl acetate): $^1H$ NMR ($CDCl_3$) δ 1.92-2.06 (4H, m), 2.44-2.48 (1H, m), 2.74-2.94 (3H, m), 3.06-3.28 (3H, m), 3.34-3.40 (1H, m), 7.16-7.32 (5H, m).

c) E-3-[Methylene-2-cyano]-2-benzyl-quinuclidine

To a suspension of potassium-tert-butoxide (2.2 g) in toluene (25 ml) was added diethylcyanomethyl phosphonate (2.9 ml) dropwise and the reaction mixture stirred for 1 hour. The product of part b) (0.4 g) was then added and the reaction stirred at room temperature for 12 h. Saturaturated ammonium chloride solution (50 ml) was added to quench the reaction and the aqueous layer extracted with ethyl acetate (2×50 ml). The combined organic extracts were dried ($Na_2CO_3$) and filtered and the solvent removed in vacuo. The residual oil was chromatographed on silica eluting with 50-100% ethyl acetate/petroleum ether to give the title compound as a white solid; $R_f$=0.60 (ethyl acetate) $^1H$ NMR ($CDCl_3$) δ 1.60-1.90 (4H, m), 2.54-3.10 (5H, m), 3.24-3.42 (2H, m), 3.90-4.00 (1H, m), 5.44-5.46 (1H, d), 7.16-7.40 (5H, m). Also isolated was Z-3-]methylene-2-cyano]-2-benzyl quinuclidine as a white solid; $R_f$=0.20 (ethyl acetate) $^1H$ NMR ($CDCl_3$) δ 1.64-1.92 (4H, m), 2.70-2.88 (3H, m), 2.98-3.20 (4H, m), 3.68-3.74 (1H, t), 4.80-4.82 (1H, d), 7.18-7.36 (5H, m).

d) E-3-[Methylene-2-carboxaldehyde]-2-benzyl quinuclidine

The product of part c) (0.64 g) was dissolved in anhydrous dichloromethane (20 ml) and cooled to −78° C. Diisobutylaluminium hydride (6.7 ml) was added dropwise and the reaction mixture stirred at −78° C. for 1 h. The reaction was quenched with the addition of 1N hydrochloric acid (20 ml) and the reaction mixture warmed to 0° C. and stirred for a further 20 min. The organic layer was separated and the aqueous layer extracted once more with dichloromethane (50 ml). The organic extracts were combined, dried ($Na_2CO_3$), filtered and the solvent removed in vacuo to give the title compound as an oil; $^1H$ NMR ($CDCl_3$) δ 1.64-1.96 (4H, m), 2.70-3.30 (6H, m), 3.52-3.58 (1H, m), 3.75 (1H, t), 5.82-5.86 (1H, dd), 7.12-7.34 (5H, m), 9.98 (1H, d).

e) E-3-[methylene-(3,5-bistrifluoromethylphenyl) hydroxymethyl]-2-benzyl quinuclidine To a suspension of magnesium (0.19 g) in diethyl ether was added 3,5-bis(trifluoromethyl)bromobenzene (1.4 ml) dropwise and the reaction stirred until the complete disappearance of the magnesium. The resulting dark solution was cooled to −78° C. and a solution of the product of Description 4 (0.64 g) in diethyl ether (5 ml) was added dropwise. After stirring for 15 min at −78° C., saturated ammonium chloride solution was added (30 ml) and the reaction warmed to room temperature. The aqueous layer was extracted with ethyl acetate (50 ml), the organic layer dried ($Na_2CO_3$), filtered and evaporated in vacuo to give an oil. Flash chromatography (silica, 20% methanol/ethyl acetate) provided a less polar diastereomer A ($R_f$=0.22, 20% methanol/ethyl acetate) and a more polar diastereomer B ($R_f$=0.09, 20% methanol/ethyl acetate).

Diastereomer A was a pale yellow solid; M.P. 125°-126° C. (diethyl ether/hexane): $^1H$ NMR ($CDCl_3$) δ 1.54-1.66 (1H, m), 1.72-1.90 (3H, m), 2.76-2.94 (3H, m), 3.00-3.20 (3H, m), 3.24-3.34 (1H, m), 3.66-3.74 (1H, t), 5.05-5.07 (1H, d), 5.54-5.56 (1H, d), 7.17-7.31 (5H, m), 7.74 (2H, s), 7.76 (1H, s).

The oxalate salt of diastereomer B was made by adding a solution of the free base in diethyl ether to a solution of oxalic acid in diethyl ether, and filtration of the resulting precipitate to give a white solid; M.P. 144°-146° C:. $^1H$ NMR ($d_6$-DMSO) δ 1.78-2.06 (4H, m), 2.88-2.95 (1H, dd), 3.11-3.16 (1H, dd), 3.14-3.26 (2H, m), 3.34-3.54 (3H, m), 4.32-4.40 (1H, m), 4.67-4.69 (1H, d), 5.56-5.58 (1H, d), 7.00-7.14 (5H, m), 7.86 (2H, s), 8.02 (1H, s).

The following examples illustrate pharmaceutical compositions according to the invention.

EXAMPLE 16A

Tablets containing 1-25 mg of compound

| Amount mg | | | |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 16B

Tablets containing 26-100 mg of compound

| Amount mg | | | |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 17

Parenteral injection

| | Amount mg |
|---|---|
| Compound of formula (I) | 1 to 100 mg |
| Citric Acid Monohydrate | 0.75 mg |
| Sodium Phosphate | 4.5 mg |
| Sodium Chloride | 9 mgü |
| Water for injection | to 1 ml |

The sodium phosphate, citric acid monohydrate and sodium chloride are dissolved in a portion of the water. The compound of formula (I) is dissolved or suspended in the solution and made up to volume.

EXAMPLE 18

Topical formulation

| | Amount mg |
|---|---|
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

SUBSTANCE P ANTAGONISM ASSAY

A. Receptor Expression in Monkey Kidney Cell Line (COS)

To express the cloned human neurokinin-1-receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+ (trademark, STRATAGENE, La Jolla, Calif., USA)) into the Sac II site. Transfection of 20 ug of the plasmid DNA into 10 million COS cells was achieved by electroporation in 800 μl of transfection buffer (135 mM NaCl, 1.2 mM CaCl$_2$, 1.2 mM MgCl$_2$, 2.4 mM K$_2$HPO$_4$, 0.6 mM KH$_2$PO$_4$, 10 mM glucose, 10 mM N-2-hydroxyethyl-piperazine-N'-2-ethane acid (HEPES) pH 7.4) at 260 V and 950 μF using the IBI GENEZAPPER (trademark IBI, New Haven, Conn., USA). The cells were incubated in 10% fetal calf serum, 2 mM glutamine, 100 U/ml penicillin-streptomycin, and 90% DMEM media (GIBCO, Grand Island, N.Y., USA) in 5% CO$_2$ at 37° C. for three days before the binding assay.

B.

Stable Expression in Chinese Hamster Ovarian Cell Line

To establish a stable cell line expressing cloned human NKIR1R, the cDNA was subcloned into the vector pRcCMV (INVITROGEN). Transfection of 20 ug of the plasmid DNA into CHO cells was achieved by electroporation in 800 μl of transfection buffer supplemented with 0.625 mg/ml Herring sperm DNA at 300 V and 950 μF using the IBI GENEZAPPER (IBI). The transfected cells were incubated in CHO media [10% fetal calf serum, 100 U/ml penicillin-streptomycin, 2 mM glutamine, 1/500 hypoxanthine-thymidine (ATCC), 90% IMDM media (JRH BIOSCIENCES, Lenexa, Kans. USA), 0.7 mg/ml G418 (GIBCO)] in 5% CO$_2$ at 37° C. until colonies were visible. Each colony was separated and propagated. The cell clone with the highest number of human NK1R was selected for subsequent applications such as drug screening.

C.

Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavellette, N.J.) and resuspended in appropriate volume of the binding buffer (50 mM Tris pH 7.5, 5 mM MnCl$_2$, 150 mM NaCl, 0.04 mg/ml bacitracin, 0.004 mg/ml leupeptin, 0.2 mg/ml BSA, 0.01 mM phosphoramidon) such that 200 μl of the cell suspension would give rise to about 10,000 cpm of specific $^{125}$I-SP binding (approximately 50,000 to 200,000 cells). In the binding assay, 200 μl of cells were added to a tube containing 20 μl of 1.5 to 2.5 nM of $^{125}$I-SP and 20 μl of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM MnCl$_2$, 150 mM NaCl) three times and its radioactivity was determined by gamma counter.

The activation of phospholiphase C by NK1R may also be measured in CHO cells expressing the human NK1R by determining the accumulation of inositol monophosphate which is a degradation product of IP$_3$. CHO cells are seeded in 12-well plate at 250,000 cells per well. After incubating in CHO media for 4 days, cells are loaded with 5 μCi of $^3$H-myoinositol in 1ml of media per well by overnight incubation. The extracellular radioactivity is removed by washing with phosphate buffered saline. LiCl is added to the well at final concentration of 10 mM with or without the test compound, and incubation is continued at 37° C. for 15 min. substance P is added to the well at final concentration of 0.3 nM to activate the human NK1R. After 30 min of incubation at 37° C., the medium is removed and 0.1N HCl is added. Each well is sonicated at 4° C. and extracted with CHCl$_3$/methanol (1:1). The aqueous phase is applied to a 1 ml Dowex AG 1X8 ion exchange column. The column is washed with 0.1N formic acid followed by 0.025M ammonium formate-0.1N formic acid.

The inositol monophosphate is eluted with 0.2M ammonium formate-0.1N formic acid and quantitated by beta counter.

The data in Table 1 were obtained for compounds of formula (I):

TABLE 1

SUBSTANCE P ANTAGONISM RESULTS

| Compound of Ex # | IC$_{50}$ @ NK1R (nM) |
|---|---|
| 1 (ISOMER A) | 50 |
| 1 (ISOMER B) | 130 |
| 2 (ISOMER B) | 197 |
| 3 (ISOMER A) | 30 |
| 3 (ISOMER B) | 110 |
| 4 (ISOMER B) | 200 |
| 5 | 170 |
| 6 | 100 |
| 7 | >300 |
| 8 | 190 |
| 9 (ISOMER A) | 0.9 |
| 9 (ISOMER B) | NT |
| 10 | 5 |
| 11 | 9 |
| 12 | 140 |
| 13 | 13 |
| 14 | 90 |
| 15 (DIASTEREOMER A) | 63 |
| 15 (DIASTEREOMER B) | 6 |

(NT = not tested)

We claim:

1. A compound of formula (IC), or a salt or prodrug thereof:

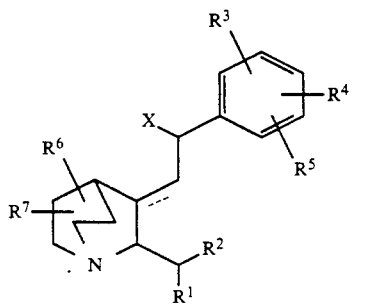

wherein
the dotted line represents an optional double bond;
X is selected from H, —OH, =O and halo;
R$^1$ is selected from H, phenyl and thienyl, which phenyl or thienyl groups may be optionally substituted by a substituent selected from halo and trifluoromethyl;
R$^2$ is selected from phenyl, thienyl and benzyl, any of which groups may be optionally substituted by a substituent selected from halo and trifluoromethyl;
R$^3$, R$^4$ and R$^5$ are independently selected from H, C$_{1-6}$ alkyl, C$_{2-6}$ alkenyl, C$_{2-6}$ alkynyl, halo, cyano, nitro, trifluoromethyl, trimethylsilyl, —OR$^a$, SR$^a$, SOR$^a$, SO$_2$R$^a$, —NR$^a$R$^b$, —NR$^a$COR$^b$, —NR$^a$CO$_2$R$^b$, —CO$_2$R$^a$ and —CONR$^a$R$^b$;
R$^6$ and R$^7$ independently represent H, C$_{1-4}$ alkyl, C$_{2-4}$ alkenyl, C$_{2-4}$ alkynyl, halo, hydroxy, C$_{1-4}$ alkoxy, carboxy or (C$_{1-4}$ alkoxy)carbonyl; or R$^6$ and R$^7$ together represent carbonyl; and
R$^a$ and R$^b$ are independently selected from H, and C$_{1-6}$ alkyl, phenyl and trifluoromethyl.

2. A compound according to claim 1 wherein R$^1$ and R$^2$ are independently selected from phenyl and thienyl, and R$^2$ may also be benzyl, any of which groups may be substituted by a substituent selected from halo and trifluoromethyl.

3. A compound according to claim 1 wherein X is halo.

4. A compound according to claim 1 wherein X is selected from H, —OH and =O; R$^1$ is H; R$^2$ is selected from phenyl or thienyl, which groups may be substituted by a substituent selected from halo and trifluoromethyl; R$^3$, R$^4$ and R$^5$ are independently selected from H, C$_{1-6}$alkyl, C$_{2-6}$alkenyl, C$_{2-6}$alkynyl, halo, cyano, nitro, trifluoromethyl, —OR$^a$, SCH$_3$, SOCH$_3$, SO$_2$CH$_3$, NR$^a$R$^b$, —NR$^a$COR$^b$, —NR$^a$CO$_2$R$^b$, —CO$_2$R$^a$ and —CONR$^a$R$^b$.

5. A compound according to claim 1 wherein X is selected from H, —OH or =O; R$^1$ and R$^2$ are independently selected from phenyl and thienyl, and R$^2$ may also be benzyl, any of which groups may be substituted by a substituent selected from halo and trifluoromethyl; R$^3$, R$^4$ and R$^5$ are independently selected from H, C$_{1-6}$alkyl, C$_{2-6}$alkenyl, C$_{2-6}$alkynyl, halo, cyano, nitro, trifluoromethyl, —OR$^a$, SCH$_3$, SOCH$_3$, SO$_2$CH$_3$, NR$^a$R$^b$, —NR$^a$COR$^b$, —NR$^a$CO$_2$R$^b$, —CO$_2$R$^a$ and —CONR$^a$R$^b$.

6. A compound according to claim 1 wherein X is hydroxy.

7. A compound according to claim 1 wherein the double bond is present; R$^1$ is selected from H and phenyl; R$^2$ is phenyl; and R$^6$ and R$^7$ are both hydrogen.

8. A compound according to claim 1 selected from:
E-3-[methylene(2-methoxyphenyl)hydroxymethyl]-2-benzhydryl quinuclidine;
E-3-[methylene(4-fluorophenyl)hydroxymethyl]-2-benzhydryl quinuclidine;
E-3-[methylene(3-trifluoromethylphenyl)hydroxymethyl]-2-benzhydryl quinuclidine;
E-3-[methylene(hydroxymethyl)phenyl]-2-benzhydryl quinuclidine;
E-3-[methylenebenzyl]-2-benzhydryl quinuclidine;
E-3-[methylene(3-trifluoromethyl)benzyl]-2-benzhydryl quinuclidine;
E-3-[methylene(3,5-bistrifluoromethylphenyl)oxo]-2-benzhydryl quinuclidine;
E-3-[methyleneketophenyl]-2-benzhydryl quinuclidine
E-3-[methylene(3,5-bistrifluoromethylphenyl) hydroxymethyl]-2-benzhydryl quinuclidine;
E-3-[methylene(3,5-bistrifluoromethylphenylfluoro)methyl]-2-benzhydryl quinuclidine;
E-3-[methylene-2-keto(3,5-dimethyl)phenyl]-2-benzhydryl quinuclidine;
E-3-[methylene(3,5-dimethylphenyl)hydroxymethyl]-2-benzhydryl quinuclidine;
E-3-[methylene(2,6-dimethylphenyl)hydroxymethyl]-2-benzhydryl quinuclidine;
E-3-[methylene(3,5-bistrifluoromethylphenylfluoro) hydroxymethyl]-2-benzhydryl quinuclidine;
or a pharmaceutically acceptable salt or a prodrug thereof.

9. A pharmaceutical composition for the treatment or prevention of a physiological disorder associated with an excess of tachykinins, comprising a compound according to claim 1 in association with a pharmaceutically acceptable carrier therefor.

10. A method for the treatment or prevention of a physiological disorder associated with an excess of tachykinins, which method comprises administration to a patient in need thereof of a tachykinin-reducing amount of a compound according to claim 1.

11. A method according to claim 10 for the treatment or prevention of pain or inflammation.

12. A method according to claim 10 for the treatment or prevention of migraine.

* * * * *